US006991786B1

(12) United States Patent
Filutowicz

(10) Patent No.: US 6,991,786 B1
(45) Date of Patent: Jan. 31, 2006

(54) ANTI-MICROBIAL BIOTHERAPEUTIC AGENTS: ALTERNATIVES TO CONVENTIONAL PHARMACEUTICAL ANTIBIOTICS

(75) Inventor: Marcin S. Filutowicz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/651,290

(22) Filed: Aug. 30, 2000

(51) Int. Cl.
*A61K 48/00* (2006.01)
*A01N 63/00* (2006.01)
*C12P 1/00* (2006.01)
*C12P 39/00* (2006.01)
*C12N 15/00* (2006.01)

(52) U.S. Cl. ............... 424/93.2; 424/93.4; 424/41; 424/42; 424/320.1

(58) Field of Classification Search ............... 424/93.2, 424/93.4; 435/41, 42, 320.1
See application file for complete search history.

(56) References Cited

U.S. PATENT DOCUMENTS

| 5,399,496 | A | * | 3/1995 | Fujiwara et al. | ........... 435/69.1 |
| 5,434,065 | A | * | 7/1995 | Mahan et al. | ................. 435/6 |
| 6,019,984 | A | * | 2/2000 | MacInnes et al. | ....... 424/255.1 |
| 6,254,874 | B1 | * | 7/2001 | Mekalanos et al. | ...... 424/234.1 |
| 6,716,631 | B1 | * | 4/2004 | delCardayre et al. | ....... 435/440 |
| 6,780,405 | B1 | * | 8/2004 | Curtiss et al. | ............. 424/93.1 |

FOREIGN PATENT DOCUMENTS

EP          0109150 A2 * 5/1984

OTHER PUBLICATIONS

Roberts et al, Journal of Bacteriology, Nov. 1990, 172 (11), p. 6204-6216.*
Klimke et al, Journal of Bacteriology, Aug. 1998, 180 (16)p. 4036-4043.*
Ambrozic et al, Microbiology, Feb. 1998, 144 (Pt. 2), p. 343-352.*
Metcalf et al, Plasmid, 1996, 35, p. 1-13.*
Rahal et al, Annales de microbiologie, 1978, 129 (4), P. 40-414.*
Toukdarian et al, Gene 223, p. 205-211.*
Ambrozic et al, Microbiology (England), Feb. 1998, 144 (Pt2), p. 343-352.*
Roberts et al, Journal of Bacteriology, Nov. 1990, 172 (11), p. 6204-6216.*
Klimke et al, Journal of Bacteriology, Aug. 1998, 180 (16), p. 4036-4043.*
Rahal et al, Annales de microbiologie (France), May-Jun. 1978, 129 (4), p. 409-414.*
Metcalf et al, Plasmid. Jan. 1996;35(1):1-13.*
Kaniga et al, Gene 109, 1991, 137-141.*
Filutowicz, M. and Rakowski, S.A., Regulatory implications of protein assemblies at the γ origin of plasmid R6K—a review. Gene 223:195-204 (1998).
Kudva, I.T. et al., Biocontrol of *Escherichia coli* O157 with O157-Specific Bacteriophages. Applied and Environmental Microbiology 65:3767-3773 (1999).
Lessl, M. and Lanka, E., Common Mechanism in Bacterial Conjugation and Ti-Mediated T-DNA Transfer to Plant Cells. Cell 77:321-324 (1994).
Molin, S. et al., Runaway Replication of Plasmid R1 Is Not Caused by Loss of Replication Inhibator Activity of Gene *cop*. Journal of Bacteriology 143:1046-1048 (1980).
Reid, G., The Scientific Basis for Probiotic Strains of *Lactobacillus*. Applied and Environmental Microbiology 65:3763-3766 (1999).
Rodriguez, M. et al., Lethality and Survival of *Klebsiella oxytoca* Evoked by Conjugative IncN Plasmids. Journal of Bacteriology 177:6352-6361 (1995).
Smith, H.W. and Huggins, M.B., Successful Treatment of Experimental *Escherichia coli* Infections in Mice Using Phage: its General Superiority over Antibiotics. Journal of General Microbiology 128:307-318 (1982).
Smith, H.W. and Huggins, M.B., Effectiveness of Phages in Treating Experimental *Escherichia coli* Diarrhoea in Calves, Piglets and Lambs. Journal of General Microbiology 129: 2659-2675 (1983).
Smith, H.W. et al., The Control of Experimental *Escherichia coli* Diarrhoea in Calves by Means of Bacteriophages. Journal of General Microbiology 133:1111-1126 (1987).
Toukdarian, A.E. and Helsinki, D.R., TrfA dimers play a role in copy-number control of RK2 replication. Gene 223:205-211 (1998).
Blasina, A., et al., "Copy-up mutants of the plasmid RK2 replication initiation protein are defective in coupling RK2 replication origins," *Proc. Natl. Acad. Sci. USA*, Apr. 1996, 93, 3559-3564.
Diaz, E., et al., "Universal barrier to lateral spread of specific genes among microorganisms," *Molecular Microbiology*, XP 000579401, 1994, 13(5), 855-861.
Haugan, K. et al., "The Host Range of RK2 Minimal Replicon Copy-Up Mutants Is Limited by Species-Specific Differences in the Maximum Tolerable Copy Number", *Plasmid*, 1995, 33, 27-39.

* cited by examiner

*Primary Examiner*—Mark Navarro
*Assistant Examiner*—Vanessa L. Ford
(74) *Attorney, Agent, or Firm*—Quarles & Brady LLP

(57) ABSTRACT

Novel antimicrobial agents that can serve as replacements to conventional pharmaceutical antibiotics are disclosed. The antimicrobial agents comprise conjugatively transmissible plasmids that kill targeted pathogenic bacteria, but are not harmful to donor bacteria. Two types of lethal transmissible plasmids are disclosed. One type kills recipient bacteria by unchecked ("runaway") replication in the recipient cells and is prevented from occurring in donor cells. Another type kills recipient bacteria by expressing a gene that produces a product detrimental or lethal to recipient bacterial cells, that gene being prevented from expression in donor cells.

24 Claims, 2 Drawing Sheets

ANTI-MICROBIAL BIOTHERAPEUTIC AGENTS: ALTERNATIVES TO CONVENTIONAL PHARMACEUTICAL ANTIBIOTICS

Pursuant to 35 U.S.C. §202(c), it is acknowledged that the United States government has certain rights in the invention described herein, which was made in part with funds from the National Institutes of Health, Grant No. GM40314.

FIELD OF THE INVENTION

The present invention relates to the field of bacteriology. In particular, the invention relates to novel antimicrobial agents comprising transmissible plasmids that kill targeted recipient bacteria, but are not harmful to donor bacteria.

BACKGROUND OF THE INVENTION

Various scientific and scholarly articles are referenced in parentheses throughout the specification. These articles are incorporated by reference herein to describe the state of the art to which this invention pertains.

As the use of conventional pharmaceutical antibiotics (herein referred to as antibiotics) increases for medical, veterinary and agricultural purposes, the increasing emergence of antibiotic-resistant strains of pathogenic bacteria is an unwelcome consequence. This has become of major concern inasmuch as drug resistance of bacterial pathogens is presently the major cause of failure in the treatment of infectious diseases. Indeed, people now die of certain bacterial infections that previously could have been easily treated with existing antibiotics. Such infections include, for instance, *Staphylococcus pneumoniae*, causing meningitis; *Enterobacter* sp., causing pneumonia; *Enterococcus* sp., causing endocarditis, and *Mycobacterium tuberculosis*, causing tuberculosis.

The emergence of single- or multi-drug resistant bacteria results from a gene mobilization that responds quickly to the strong selective pressure that is a consequence of antibiotic uses. Over the last several decades, the increasingly frequent usage of antibiotics has acted in concert with spontaneous mutations arising in the bacterial gene pool to produce antibiotic resistance in certain strains. This gene pool is continually utilized by previously sensitive strains capable of accessing it by various means including the transfer of extrachromosomal elements (plasmids) by conjugation. As a result, single- and multi-drug resistance mutations are commonly found in a large variety of bacterial plasmids.

Presently there is no known method by which to avoid the selection of antibiotic resistant bacterial mutants that arise as a result of the many standard applications of antibiotics in the modern world. Accordingly, a need exists to develop alternative strategies of antibacterial treatment.

Interest in the use of bacteriophages to treat infectious bacterial diseases developed early in the twentieth century, and has undergone a resurgence in recent years. For instance, bacteriophages have been shown effective in the treatment of certain pathogenic *E. coli* species in laboratory and farm animals, and have been proposed as a viable alternative to the use of antibiotics (Smith & Huggins, J. Gen. Microbiol. 128: 307–318, 1981; Smith & Huggins, J. Gen. Microbiol. 129: 2659–2675, 1983; Smith et al., J. Gen. Microbiol. 133: 1111–1126, 1986; Kuvda et al., Appl. Env. Microbiol. 65: 3767–3773, 1999). However, the use of bacteriophages as antimicrobial agents has certain limitations. First, the relationship between a phage and its host bacterial cell is typically very specific, such that a broad host-range phage agent generally is unavailable. Second, the specificity of interaction usually arises at the point of the recognition and binding of phage to the host cell. This often occurs through the expression of surface receptors on the host cell to which a phage specifically binds. Inasmuch as such receptors are usually encoded by a single gene, mutations in the host bacterial cell to alter the surface receptor, thereby escaping detection by the phage, can occur with a frequency equivalent to or higher than, the mutation rate to acquire antibiotic resistance. As a result, if phage were utilized as commonly as antibiotics, resistance of pathogenic bacteria to phages could become as common a problem as antibiotic resistance.

Another approach to controlling pathogenic bacteria has been proposed, which relies on using molecular biological techniques to prevent the expression of antibiotic resistance genes in pathogenic bacteria (U.S. Pat. No. 5,976,864 to Altman et al.). In this method, a nucleic acid construct encoding an "external guide sequence" specific for the targeted antibiotic resistance gene is introduced into the pathogenic bacterial cells. The sequence is expressed, hybridizes with messenger RNA (mRNA) encoding the antibiotic resistance gene product, and renders such mRNA sensitive to cleavage by the enzyme RNAse P. Such a system also has limited utility, since it is targeted to specific antibiotic resistance genes. While the system may be effective in overcoming resistance based on expression of those specific genes, continued use of the antibiotics places selective pressure on the bacteria to mutate other genes and develop resistance to the antibiotic by another mechanism.

It is clear from the foregoing discussion that current alternatives to antibiotic use are limited and suffer many of the same drawbacks as antibiotic use itself. Thus, a need exists for a method of controlling pathogenic bacteria that is flexible in range and that cannot be overcome by the bacteria by a single small number of mutations.

SUMMARY OF THE INVENTION

The present invention provides novel antibacterial agents that are efficiently transferred to pathogenic bacteria, which have a flexible range, and to which the target bacteria have difficulty developing resistance. These antibacterial agents offer an effective alternative to the use of conventional antibiotics.

According to one aspect of the invention, an antibacterial agent is provided which comprises a non-pathogenic donor bacterial cell harboring at least one transmissible plasmid having the following features: (a) an origin of replication for synthesizing the plasmid's DNA in a bacterial cell, wherein initiation of replication at the origin of replication is negatively controlled by a plasmid replication repressor; (b) an origin of transfer to provide the initiation site for conjugative transfer of the transmissible plasmid from the donor cell to at least one recipient cell; and (c) at least one selectable marker gene. The donor bacterial cell further comprises one or more conjugative transfer genes conferring upon the donor cell the ability to conjugatively transfer the transmissible plasmid to the recipient cell. The donor cell also produces the plasmid replication repressor. The recipient cell is a pathogenic bacterium that does not produce the plasmid replication repressor.

According to another aspect of the invention, a different antibacterial agent is provided which comprises a non-pathogenic donor bacterial cell harboring at least one transmissible plasmid having these following features: (a) an origin of replication for synthesizing the plasmid's DNA in a bacterial cell; (b) an origin of transfer to provide the start site for conjugative transfer of the transmissible plasmid from the donor cell to at least one recipient cell; and (c) at least one killer gene that, upon expression in a bacterial cell, produces a product that kills the cell. The donor cell again comprises one or more transfer genes conferring upon the donor cell the ability to conjugatively transfer the transmissible plasmid to the recipient cell, and is modified so as to be unaffected by the product of the killer gene. The recipient cell is a pathogenic bacterium that has not been modified so as to be unaffected by the product of the killer gene.

The present invention also provides methods of treating a patient for a pathogenic bacterial infection which comprises administering to the patient one of the aforementioned antibacterial agents. The mode of administration is selected to ensure that the donor cells of the antibacterial agent come into conjugative proximity to the pathogenic bacterial cells, such that the transmissible plasmids of the donor cells are conjugatively transferred from the donors to the pathogenic cells. Following conjugation and dependent upon the nature of the plasmid, it either undergoes unchecked replication or the at least one killer gene is expressed to produce a gene product that is detrimental or lethal to the pathogenic bacterial cells.

The present invention also provides pharmaceutical preparations for treating a patient for a bacterial infection. These preparations comprise one of the aforementioned antibacterial agents, formulated for a pre-determined route of administration to the patient.

Other features and advantages of the present invention will be understood by reference to the drawings, detailed description and examples that follow.

DETAILED DESCRIPTION OF THE INVENTION

Figure 1:
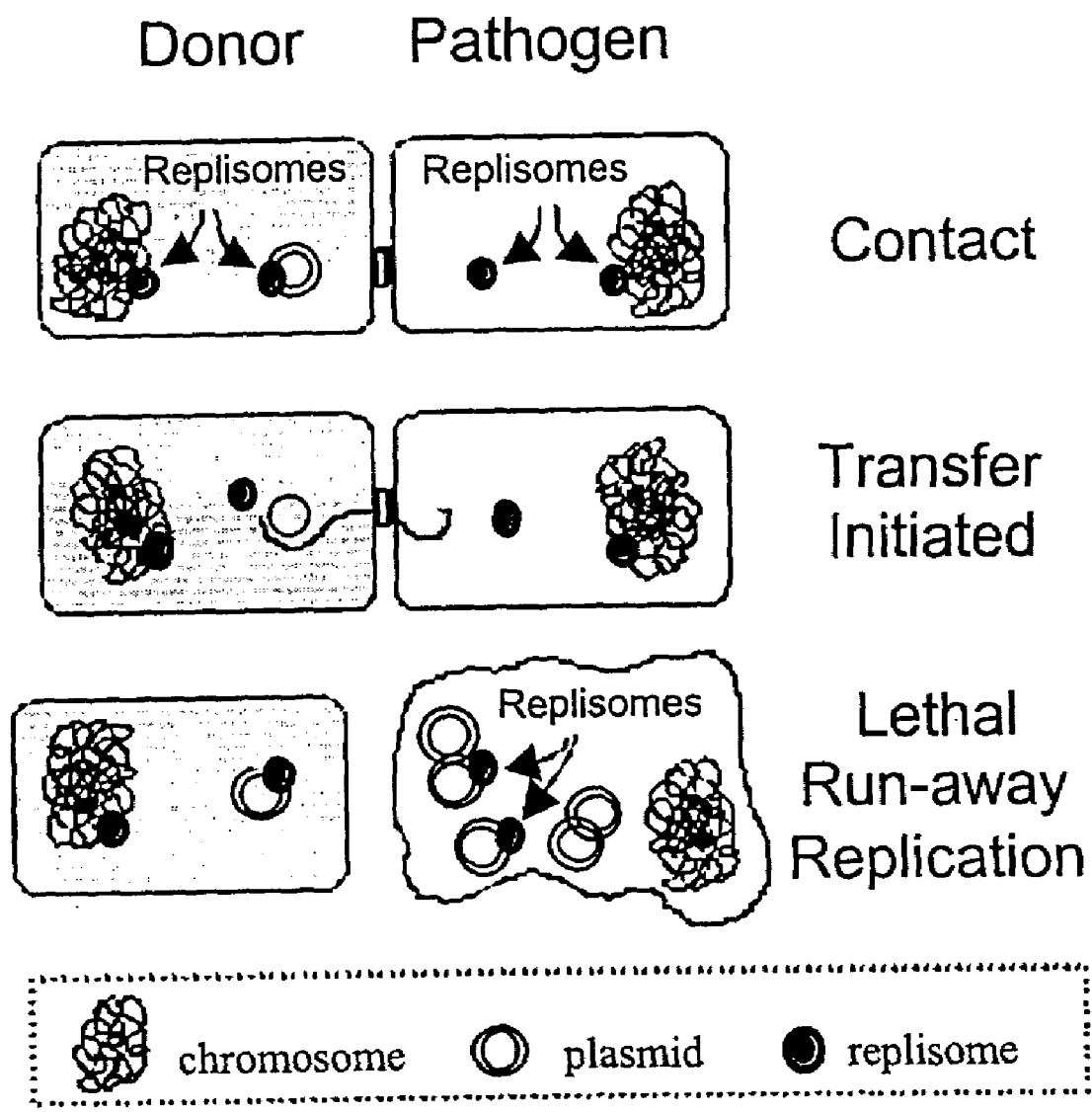
FIG. 1. Schematic diagram showing process of killing pathogenic bacteria by conjugative transfer of plasmids that engage in runaway replication in the recipient cells.

The present invention provides novel antibacterial strategies that utilize the highly efficient bacterial conjugation system to transfer a "killer" plasmid from a donor cell that is engineered to be immune to the killer plasmid, to a target bacterial cell that is not.

In one aspect of the invention, the "killer plasmid" is one that undergoes runaway replication in the recipient cells, ultimately killing the cells. The basic principles underlying the mechanism by which runaway plasmid replication kills cells are outlined below.

Plasmids are dispensable DNA molecules that are stably maintained in bacterial populations. Plasmids replicate extra-chromosomally inside the bacterium and can transfer their DNA from one cell to another by a variety of mechanisms. DNA sequences controlling extra-chromosomal replication (ori) and transfer (tra) are distinct from one another; i.e., a replication sequence cannot control plasmid transfer, and vice-versa. Replication and transfer are both complex molecular processes that require plasmid- and host-encoded functions.

Bacterial conjugation is the unidirectional and horizontal transmission of information from one bacterium to another. The genetic material transferred may be a plasmid or it may be part of a chromosome. Bacterial cells possessing a conjugative plasmid contain a surface structure (the sex pilus) that is involved in the coupling of donor and recipient cells, and the transfer of the genetic information. Conjugation requires contact between cells, and it is clear that the transfer of genetic traits can be mediated by many plasmids in a process which involves the physical transfer of DNA from a donor to a recipient cell.

Among all natural transfer mechanisms, conjugation is the most efficient. The conjugative process permits the protection of plasmid DNA against environmental nucleases, and the very efficient delivery of plasmid DNA into a recipient cell.

Conjugation functions are plasmid encoded. Numerous conjugative plasmids (and transposons) are known, which can transfer associated genes within one species (narrow host range) or between many species (broad host range). Transmissible plasmids have been reported in numerous Gram-positive genera including pathogenic strains of *Streptococcus, Staphylococcus, Bacillus, Clostridium* and *Nocardia*. The early stages of conjugation differ in Gram-negative and Gram-positive bacteria. As mentioned the role of some of the transfer genes in conjugative plasmids from Gram-negative bacteria is to provide pilus-mediated cell-to-cell contact, formation of a conjugation pore and related morphological functions. The pili do not appear to be involved in initiating conjugation in Gram-positive bacteria. The feature best understood in the enterococci is the involvement of pheromones. Pheromones are hydrophobic polypeptides of 7–8 amino acids produced by potential recipient cells. Pheromones invite attention of potential donor cells containing conjugative plasmids. PAD1 is one of the best studied pheromone-induced plasmids which can replicate in 50 different bacterial hosts in addition to *Enterococcus faecelis* strains from which it was initially isolated (Clewel, D. B. 1999. Sex pheromone systems in Enterococci, In: Cell—Cell Signaling in Bacteria, Ed. G. M. Dunny, S. C. Winans; ASM, Washington D. C. pp 47–65). Moreover, conjugation can occur between genera as widely diverse as anaerobes and aerobes.

Naturally occurring plasmids are present within host cells at a characteristic concentration (referred to herein as a particular plasmid's "copy number"). Of great significance to the present invention is the fact that plasmid copy number is negatively controlled. Thus, mutations that destroy the elements of the negative control cause an over-replication phenotype that manifests itself by an increase in the plasmid's copy number ("copy-up" phenotype). In extreme cases of copy-up mutations, plasmid replication is completely unchecked due to the loss of copy control mechanisms. This is referred to as "runaway plasmid replication" or simply "runaway replication."

Runaway plasmid replication is lethal for the host cell. This is because, although the plasmid encodes the replication (Rep) protein that controls its copy number, all other replication proteins are encoded by chromosomal genes. These chromosomally encoded proteins assemble into a complex called a replisome. A typical bacterial cell possesses a small, fixed number of replisomes. Because both the chromosome and the plasmids require the same replisomes for DNA synthesis, an excess of plasmids acts like a trap to occupy all of the cell's replisomes. This results in the inability of the cell's chromosome to replicate, ultimately leading to the death of the host cell.

The use of runaway replication plasmids as a means to kill recipient cells has a number of advantages over conventional antibiotic methodologies. One significant advantage is that, since the entire host replication machinery is targeted, multiple mutations would be required to avoid death by elevating the expression or activity of the replisome sub-assemblies. For instance, mutations in ten genes would be required just to increase the amount or activity of DNA polymerase III holoenzyme (composed of ten different sub-units), and this polymerase is just one of the replisome's sub-assemblies. Thus, there is little or no chance of a bacterium acquiring resistance to being killed by over-replicating plasmids. In contrast, conventional antibiotics typically inhibit only a single enzymatic activity that is essential for the cell's survival. A single-target strategy unavoidably leads to the quick acquisition of resistance to such drugs, caused by the relatively high spontaneous mutation frequency for one gene ($10^{-6}$ to $10^{-8}$).

Because runaway replication mutations are lethal to the host cell, donor cells that maintain such plasmids must be engineered so that replication control is restored. This is accomplished by providing the wild-type Rep protein to the host cell, either on another plasmid or by integration into the bacterial chromosome using standard homologous recombination techniques.

Thus, the runaway replication plasmid, antibacterial strategy of the invention comprises the following basic components:

(1) a plasmid that, alone or with the assistance of a helper plasmid, comprises the genes necessary to effect conjugative transfer of the plasmid from a donor cell to a recipient cell; the replication of the plasmid is negatively controlled by a gene that can be de-activated (via mutation) so as to release the negative control on plasmid replication (referred to as a "runaway replication plasmid");

(2) optionally, a helper plasmid with the requisite conjugative transfer genes; and (3) a donor cell for maintaining the runaway replication plasmid in a replication-suppressed state, so as not to be killed by the plasmid.

A number of conjugative plasmids have been well characterized, and can serve as subjects for mutagenesis to create runaway mutants, which may be used in embodiments of the present invention. Such mutants contain all components needed for conjugative self-transfer from donor to recipient cells but are defective in their replicative repressor (Rep) function. Examples of such mutants, both broad-range and narrow-range, are known in the art (Haugan et al., Plasmid 33: 27–39, 1995; Molin et al., J. Bacteriol. 143: 1046–1048, 1980; Toukdarian & Helinski, Gene 223: 205–211, 1998). A particularly preferred plasmid of this type is a mutant of plasmid R6K, as described in detail in Examples 1 and 2. Other examples include, but are not limited to, RK2, pCU1, p15A, pIP501, pAMPβ1 and pCRG1600.

As an alternative to the use of mutants, it may sometimes be preferable to use various components of conjugative plasmids whose features are well understood, to create plasmids having all necessary features. Features required on runaway replication plasmids or helper plasmids include (1) an origin of replication (oriV herein), the sequence from which replication of the plasmid originates and the sequence that is negatively regulated by a Rep protein; (2) an origin of transfer (oriT herein), the sequence from which the conjugal plasmid transfer originates; (3) the transfer (tra) genes required in trans to effect conjugation; and (4) a screenable marker gene that would function in a donor but not in the recipient cells. The donor cell containing the runaway replication plasmid is engineered to contain a functional repressor (Rep) of replication at oriV, thereby controlling replication of the runaway replication plasmid while it is still in the donor.

Figure 2A:
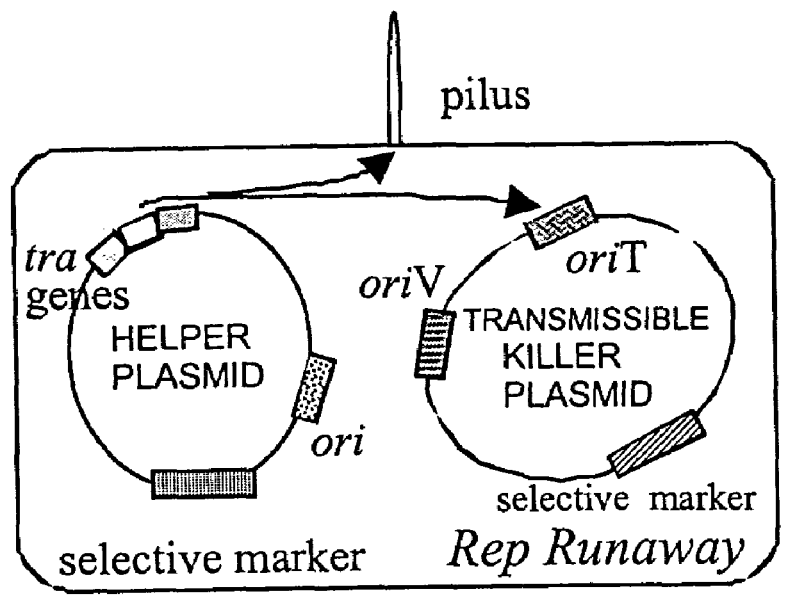
FIG. 2A. Schematic diagram of a non-self-transmissible, runaway replication plasmid system using a helper plasmid and a transmissible runaway replication plasmid.
Figure 2B:
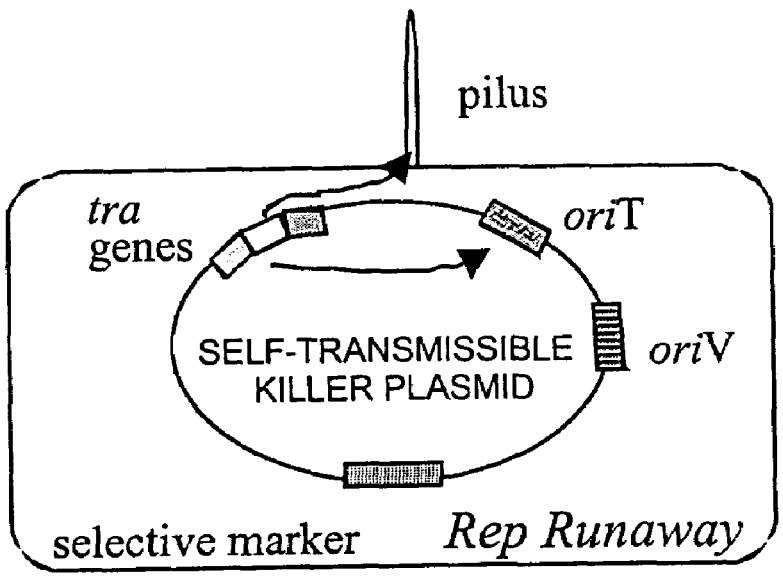
FIG. 2B. Schematic diagram of a self-transmissible, runaway replication plasmid system.

Two basic systems are contemplated: a non-self-transmissible plasmid system and a self-transmissible plasmid system. These are shown schematically in FIGS. 2A and 2B.

In the non-self-transmissible system (FIG. 2A), the runaway replication plasmid contains an oriT, an oriV and a screenable marker gene. The helper plasmid contains the additional tra genes, along with its own origin of replication and a selective marker. Thus, the helper plasmid enables conjugative transfer of the runaway replication plasmid, but is itself confined to the donor cell due to its lack of an oriT. Since the runaway replication plasmid lacks the necessary tra genes to convert the recipient cell into a donor cell, the cycle of conjugation ends with the original recipient cell. It cannot transfer its runaway replication plasmid to a second recipient before it dies. In the self-transmissible system (FIG. 2B), the runaway replication plasmid contains an oriT, an oriV and a screenable marker gene. It also contains the additional tra genes needed for conjugative transfer. Thus, unlike the non-self-transmissible plasmid described above, once this plasmid has been transmitted from the original donor to a first recipient, it is capable of transmitting itself again to subsequent recipients before the first recipient cell is killed by runaway replication. A plasmid of this type has the capability of much faster dissemination among recipient cells than the non-self-transmissible type, resulting in faster and more widespread killing of those cells.

In either the self-transmissible or the self-non-transmissible system, the donor cells must contain a gene encoding a functional Rep protein that represses plasmid replication initiated at oriV. The Rep-encoding gene is typically integrated into the donor genomic DNA. Plasmid DNA comprising the Rep-encoding gene is introduced into bacterial cells by any commonly known technique (e.g., transformation). The Rep-encoding gene can be integrated into the host genome by a site-specific recombination, according to standard methods (Li-Ch Huang, E. Wood and M. Cox; J. Bacteriol. 179: 6076–6083, 1997).

A number of bacterial oriV's and the Rep proteins that negatively control them have been characterized. Each of these is contemplated for use in the present invention. Examples of suitable oriV/Rep systems for use in the invention include, but are not limited to: RK2, R6K, rts 1, p15A, RSF1010, F and P1.

The selection of oriV will confer on the system its range of potential recipients for runaway replicating plasmids. In most instances it may be preferable to target a specific pathogen as recipient of the runaway replication plasmid. Such instances include, but are not limited to using the conjugative runaway plasmids for combating Enterobacteria, Enterococci, Staphylococci and non-sporulating Gram-positive pathogens such as *Nocardia* and *Mycobacterium* sp. Examples of selective host range plasmids from which such oriV's may be obtained include, but are not limited to, P1 and F.

In instances where it is desirable to affect a wide variety of pathogenic recipients, a broad range oriV is employed. Examples of broad range ("promiscuous") plasmids from which oriV's may be obtained include, but are not limited to: R6K, RK2, p15A and RSF1010.

As used herein, the term "range" (or "host range") refers generally to parameters of both the number and diversity of different bacterial species in which a particular plasmid (natural or recombinant) can replicate. Of these two parameters, one skilled in the art would consider diversity of organisms as generally more defining of host range. For instance, if a plasmid replicates in many species of one group, e.g., Enterobacteriaceae, it may be considered to be of narrow host range. By comparison, if a plasmid is reported to replicate in only a few species, but those species are from phylogenetically diverse groups, that plasmid may be considered of broad host range. As discussed above, both types of plasmids (or components thereof) will find utility in the present invention.

Conjugative transfer (tra) genes also have been characterized in many conjugative bacterial plasmids. The interchangeability between the gene modules conferring the ranges of hosts susceptible for conjugal transfer and vegetative replication include Gram-positive and Gram-negative species. Examples of characterized tra genes that are suitable for use in the present invention are the tra genes from: (1) F (Firth, N., Ippen-Ihler, K. and Skurray, R. A. 1996, Structure and function of F factor and mechanism of conjugation. In: *Escherichia coli* and *Salmonella*, Neidhard et al., eds., ASM Press, Washington D.C.); (2) R6K (Nunez, B., Avila, P. and de la Cruz, 1997, Genes involved in conjugative DNA processing. Mol. Microbiol. 24: 1157–1168); and (3) Ti (Ferrand, S. K., Hwang, I. and Cook, D. M. 1996, The tra region of Nopaline type Ti plasmid is a chimera with elements related to the transfer systems of RSF1010, RP4 and F. J. Bacteriol. 178: 4233–4247).

According to another aspect of the invention, the bacterial conjugation system is again utilized, this time to efficiently deliver a variety of "killer genes" to target bacterial cells. The delivery of various killer genes to bacterial cells occurs in nature, upon infection of bacteria with bacteriophages. Bacteriophages utilize a number of different mechanisms to maintain their own replication cycles, generally resulting in lysis of the host bacterial cells. Indeed, bacteriophages have been proposed and used as alternatives to antibiotics, as discussed above in the Background of the Invention. One serious drawback to the use of bacteriophages for this purpose is that they are often extremely host-specific, binding only to cell surfaces possessing specific receptors. As a result, bacteria quickly develop resistance mutations in the receptor, thereby escaping recognition by the phage. The present invention circumvents that drawback by placing the killer genes (from a phage or other source) on a conjugative plasmid. The conjugative plasmid containing the killer gene, like the conjugative runaway replication plasmids described above, is thereafter efficiently distributed to recipient cells.

Bacteriophage kill host cells by a variety of mechanisms, many of which are encoded by a discrete set of genes in the phage genome. For instance, bacteriophage MS2 contains a gene encoding a bacterial lysis protein (Coleman, J., Inouye, M. and Atkins, J. 1983. Bacteriophage MS2 lysis protein does not require coat protein to mediate cell lysis. J. Bacteriol. 153: 1098–1100). Phage T4D contains genes encoding proteins that degrade cytosine-containing DNA in bacterial host cells (Kutter, E. and Wilberg, J. 1968. Degradation of cytosine-containing bacterial and bacteriophage DNA after infection of *E. coli* B with bacteriophage T4D wild type and with mutants defective in genes 46, 47 and 56. J. Mol. Biol. 38: 395–411). Other T4 phage encode gene products that interfere with transcription of cytosine-containing DNA (Drivdahl, R. and Kutter, E. 1990. Inhibition of transcription of cytosine-containing DNA in vitro by alc gene product of bacteriophage T4. J. Bacteriol. 172: 2716–2727). Yet other T4 gene products are responsible for the disruption of the bacterial nucleoid (Bouet, J., Woszczuk, J., Repoila, F., Francois, V., Jouam, J. and Krisch, H. 1994. Direct PCR sequencing of the ndd gene of bacteriophage T4: identification of the gene product responsible for the disruption of the bacterial nucleoid. Gene 141: 9–16). Genes such as these can be inserted into a conjugative plasmid such as those described above, for efficient distribution to target recipient cells.

In addition, other types of killer genes may be utilized similarly. These include naturally-occurring or synthetic genes. A nonlimiting example of a naturally-occurring gene that is suitable for use in the invention is the hok gene product described by Gerdes et al. (Gerdes, K., Bech, F., Jorgensen S., Loebner-Olsen, A., Rasmussen, P., Atlung, T., Boe, L., Karlstrom, O., Molin S., and von Meyenburg K. 1986. Mechanism of postsegregational killing by the hok gene product of the parB system of plasmid R1 and its homology with rel F gene product of the *E. coli* relB operon. EMBO J. 5: 2023–2029). Examples of man-made nucleic acid molecules that may be used in this aspect of the invention include: (1) sequences encoding non-hemolytic P-amino acid oligomers, which are a new class of molecules based on inhibitors of Sigma-Core RNA polymerase interaction; (2) sequences encoding peptides with bactericidal activity and endotoxin neutralizing activity for Gram-negative bacteria as described in U.S. Pat. No. 5,830,860; (3) sequences encoding RNA molecules with binding affinity to critical bacterial cellular targets (e.g., Chen, H., Gold, L. 1994. Selection of high affinity RNA ligands to reverse transcriptase: Inhibition of cDNA synthesis and Rnase H activity. Biochemistry 33: 8746–8756); and (4) oligonucleotides generated by the SELEX method for the in vitro evolution of nucleic acid molecules with highly specific binding to target molecules as described in U.S. Pat. No. 5,475,096 and U.S. Pat. No. 5,270,163.

In these systems, death of the donor plasmid must be considered. It can be prevented by employing a synthetic promoter-operator system whose expression is prevented by the repressor made only in the donor cells.

Regardless of the type of killer plasmid that is utilized, the plasmid must contain a screenable marker gene. In traditional molecular biological manipulations of recombinant bacteria, the screenable marker gene is an antibiotic resistance gene. Since the present invention is designed to avoid further spread of antibiotic resistance, an alternative screenable marker system is preferred for use in the present invention. Accordingly, though antibiotic resistance markers can be used, preferred screenable markers are nutritional markers, i.e., any auxotrophic strain (e.g., Trp$^-$, Leu$^-$, Pro$^-$) containing a plasmid that carries a complementing gene (e.g., trp$^+$, leu$^+$, pro$^+$).

The donor bacterial strain for any of the above-described killer plasmids can be any one of thousands of non-pathogenic bacteria associated with the body of warm-blooded animals, including humans. Preferably, non-pathogenic bacteria that colonize the non-sterile parts of the body (e.g., skin, digestive tract, urogenital region, mouth, nasal passages, throat and upper airway, ears and eyes) are utilized as donor cells, and the methodology of the invention is used to combat bacterial infections of these parts of the body. In another embodiment, safe donors of these plasmids are developed for combating systemic infection. Examples of particularly preferred donor bacterial species include, but are not limited to: (1) non-pathogenic strains of *Escherichia* coli (*E. coli* F18 and *E. coli* strain Nissle 1917), (2) various species of *Lactobacillus* (such as *L. casei, L. plantarum, L. paracasei, L. acidophilus, L. fermentum, L. zeae* and *L. gasseri*), (3) other nonpathogenic or probiotic skin-or GI colonizing bacteria such as *Lactococcus*, Bifidobacteria, Eubacteria, and (4) bacterial mini-cells, which are anucleoid cells destined to die but still capable of transferring plasmids (see; e.g., Adler H. I., Fisher, W., D., Cohen. N., Hardigree A. A. (1970) Miniature *Escherichia coli* cells deficient in DNA. Proc, Nat. Acad, Sci USA 57; 321–326; Frazer A. C., Curtiss III, R., (1975) Production Properties and Utility of Bacterial Minicells. Current Topics in Microbiology and Immunology 69: 1–84; U.S. Pat. No. 4,968,619 to Curtiss III).

As mentioned, the target recipient cells are pathogenic bacteria dispersed throughout the body, but particularly on the skin or in the digestive tract, urogenital region, mouth, nasal passages, throat and upper airways, eyes and ears. Of particular interest for targeting and eradication are pathogenic strains of *Pseudomonas aeruginosa, Escherichia coli, Staphylococcus pneumoniae* and other species, *Enterobacter* spp., *Enterococcus* spp. and *Mycobacterium tuberculosis*. Others are also discussed herein, and still others will be readily apparent to those of skill in the art.

It is clear from the foregoing discussion that numerous types of killer plasmids (e.g., runaway replication plasmids, plasmids carrying lethal phage genes, etc.) are suitable for use in the present invention. In view of this, one of skill in the art will appreciate that a single donor bacterial strain might harbor more than one type of killer plasmid. Such multiple plasmid systems can contain a plurality of plasmids targeted to different recipient cells. Further, two or more donor bacterial strains, each containing one or more killer plasmids, may be combined for a similar multi-target effect.

Once the recombinant donor bacteria comprising the killer plasmid(s) are produced, they are used to protect against one or more selected pathogens in individuals requiring such treatment. Depending on the cell population or tissue targeted for protection, the following modes of administration of the bacteria of the invention are contemplated: topical, oral, nasal, pulmonary/bronchial (e.g., via an inhaler), ophthalmic, rectal, urogenital, subcutaneous, intraperitoneal and intravenous. The bacteria preferably are supplied as a pharmaceutical preparation, in a delivery vehicle suitable for the mode of administration selected for the patient being treated. The term "patient" or "subject" as used herein refers to humans or animals (animals being particularly useful as models for clinical efficacy of a particular donor strain).

For instance, to deliver the bacteria to the gastrointestinal tract or to the nasal passages, the preferred mode of administration is by oral ingestion or nasal aerosol, or by feeding (alone or incorporated into the subject's feed or food). In this regard, it should be noted that probiotic bacteria, such as *Lactobacillus acidophilus*, are sold as gel capsules containing a lyophilized mixture of bacterial cells and a solid support such as mannitol. When the gel capsule is ingested with liquid, the lyophilized cells are re-hydrated and become viable, colonogenic bacteria. Thus, in a similar fashion, donor bacterial cells of the present invention can be supplied as a powdered, lyophilized preparation in a gel capsule, or in bulk for sprinkling into food or beverages. The re-hydrated, viable bacterial cells will then populate and/or colonize sites throughout the upper and lower gastrointestinal system, and thereafter come into contact with the target pathogenic bacteria.

For topical applications, the bacteria may be formulated as an ointment or cream to be spread on the affected skin surface. Ointment or cream formulations are also suitable for rectal or vaginal delivery, along with other standard formulations, such as suppositories. The appropriate formulations for topical, vaginal or rectal administration are well known to medicinal chemists.

The present invention will be of particular utility for topical or mucosal administrations to treat a variety of bacterial infections or bacterially related undesirable conditions. Some representative examples of these uses include treatment of (1) conjunctivitis, caused by *Haemophilus* sp., and corneal ulcers, caused by *Pseudomonas aeruginosa*; (2) otititis externa, caused by *Pseudomonas aeruginosa*; (3) chronic sinusitis, caused by many Gram-positive cocci and Gram-negative rods; (4) cystic fibrosis, associated with *Pseudomonas aeruginosa*; (5) Enteritis, caused by *Helicobacter pylori* (ulcers), *Escherichia coli, Salmonella typhimurium, Campylobacter* and *Shigella* sp.; (6) open wounds, both surgical and non-surgical, as a prophylactic measure for many species; (7) burns to eliminate *Pseudomonas aeruginosa* or other Gram-negative pathogens; (8) acne, caused by *Propionobacter acnes*; (9) nose and skin infections caused by methicillin resistant *Staphylococcus aureus* (MSRA); (10) body odor caused mainly by Gram-positive anaerobic bacteria (i.e., use in deodorants); (11) bacterial vaginosis associated with *Gardnerella vaginalis* and other anaerobes; and (12) gingivitis and/or tooth decay caused by various organisms.

Pharmaceutical preparations comprising the donor bacteria are formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of the donor bacteria calculated to produce the desired antibacterial effect in association with the selected pharmaceutical carrier. Procedures for determining the appropriate dosage unit are well known to those skilled in the art.

Dosage units may be proportionately increased or decreased based on the weight of the patient. Appropriate concentrations for achieving eradication of pathogenic bacteria in a target cell population or tissue may be determined by dosage concentration curve calculations, as known in the art.

Other uses for the donor bacteria of the invention are also contemplated. These include agricultural and horticultural applications, such as: (1) use on meat or other foods to eliminate pathogenic bacteria; (2) use in animal feed (chickens, cattle) to reduce bio-burden or to reduce or eliminate particular pathogenic organisms (e.g., *Salmonella*); (3) use on fish to prevent "fishy odor" caused by *Proteus* and other organisms; and (4) use on cut flowers to prevent wilting.

The following examples are set forth to describe the invention in greater detail. They are intended to illustrate, not to limit, the invention. Unless otherwise specified, general cloning, microbiological, biochemical and molecular biological procedures such as those set forth in Sambrook et al., *Molecular Cloning*, Cold Spring Harbor Laboratory (1989) ("Sambrook et al.") or Ausubel et al. (eds) *Current Protocols in Molecular Biology*, John Wiley & Sons (2000) ("Ausubel et al.") are used.

EXAMPLE 1

Preparation of Runaway Replication

Plasmid from Plasmid R6K

Plasmid R6K s an *Escherichia coli* conjugative plasmid. Replication of R6K derivatives containing its oriV called γ ori requires a Rep protein, π, which is encoded by the plasmid's pir gene. π protein is bifunctional in replication; it acts as an activator of replication at low cellular levels and an inhibitor of replication at elevated levels. For a review of R6K replication and its control by π protein, see Filutowicz & Rakowski (1998) Gene 223, 195–204.

Using site-directed mutagenesis, the inventor has obtained the following three types of mutations within the pir gene:
 (1) double amino acid substitution: pro106leu, phe107ser (numbering of residues according to Stalker et al. (1982) J. Mol. Biol. 161: 33–43).
 (2) deletion of codons 106 and 107; and
 (3) deletion of codons 105, 106 and 107.

The mutated pir genes were combined with the γ ori in two locations. In one location, the mutant gene was contained on a plasmid different from the plasmid containing the γ ori, thus providing π protein in trans. In another location, the mutant pir gene was contained on the same plasmid with the γ ori, thus providing its function in cis.

EXAMPLE 2

Bacterial Cells Transformed with Plasmids

Containing Mutated pir and γ ori in cis are Killed

*Escherichia coli* cells were transformed with either (1) the plasmids containing a mutated pir gene and the γ ori in trans; or (2) a plasmid containing a mutated pir gene and the γ ori in cis.

In transformed cells containing the mutant pir and the γ ori in trans, the copy number of the γ ori plasmid was increased 20- to 25-fold in comparison to wild-type pir controls. Cells transformed with the mutant pir and the γ ori in cis were killed by the runaway replication of γ ori. The occurrence of the runaway phenotype when mutant pir is in cis to the ori but not in trans is believed to be caused by the enhanced effect of the origin activation and translation of nascent π protein occurring next to each other.

The present invention is not limited to the embodiments described and exemplified above, but is capable of variation and modification without departure from the scope of the appended claims.

I claim:

1. A recombinant donor bacterium-harboring at least one transmissible plasmid, said transmissible plasmid comprising:
 a) an origin of replication for synthesizing the plasmid in a bacterial cell, wherein initiation of replication at the origin is negatively controlled by a plasmid replication protein comprising a copy number control function, wherein in the absence of the plasmid replication protein copy number control function, the transmissible plasmid undergoes runaway replication;
 b) a mutant gene encoding a plasmid replication protein comprising a copy number control function, wherein said mutant gene encoding said plasmid replication protein comprises a mutation that reduces the copy number control function of said plasmid replication protein;
 c) an origin of transfer from which conjugative transfer of the transmissible plasmid initiates from the donor bacterium to at least one recipient bacterium;
 d) at least one screenable marker gene;
 wherein the donor bacterium further comprises one or more transfer genes conferring upon the donor bacterium the ability to conjugatively transfer the transmissible plasmid to the recipient bacterium, and wherein the donor bacterium further comprises a wild type gene encoding said plasmid replication protein comprising a copy number control function, and further wherein the at least one recipient bacterium is a pathogenic bacterium that does not produce the plasmid replication protein comprising a copy number control function, thereby enabling the transmissible plasmid to undergo runaway replication in the recipient bacterium.

2. The recombinant donor bacterium of claim 1, further comprising a helper plasmid, wherein said one or more transfer genes are contained on said helper plasmid, such that the transmissible plasmid is transmissible from the donor bacterium to a recipient bacterium, but is not further transmissible from the recipient bacterium to another recipient bacterium.

3. The recombinant donor bacterium of claim 1, wherein said one or more transfer genes are contained on the transmissible plasmid, such that the transmissible plasmid is transmissible from the donor bacterium to a recipient bacterium, and further from the recipient bacterium to another recipient bacterium.

4. The recombinant donor bacterium of claim 1, wherein said plasmid replication protein is a bifunctional protein comprising a plasmid replication activator function and a plasmid replication inhibitor function, wherein when the plasmid replication activator function is present and when the plasmid replication inhibitor function is reduced, the transmissible plasmid undergoes runaway replication, and wherein said mutant gene encoding a plasmid replication protein comprising a copy number control function is a mutant gene encoding a bifunctional plasmid replication protein comprising a plasmid replication activator function and a plasmid replication inhibitor function, wherein said gene encoding said bifunctional plasmid replication protein comprises a mutation that reduces the plasmid replication inhibitor function of said bifunctional plasmid replication protein.

5. The recombinant donor bacterium of claim 4, wherein the naturally-occurring transmissible plasmid is selected from the group consisting of RK2, R6K, pCU1, p15A, pIP501, pAMβ1 and pCRG1600.

6. The recombinant donor bacterium of claim 5, wherein the naturally-occurring transmissible plasmid is R6K and the mutation in said bifunctional plasmid replication protein comprises a mutation in the R6 K pir gene such that its encoded π protein comprises at least one amino acid deletion or substitution at amino acid 105, 106 or 107.

7. The recombinant donor bacterium of claim 1, wherein the donor bacterium is a non-pathogenic strain of bacteria selected from the group consisting of *Escherichia coli, Lactobacillus* spp., *Lactococcus*, Bifidobacteria, Eubacteria, and bacterial minicells.

8. The recombinant donor bacterium of claim 1, wherein the recipient bacterium is a pathogenic strain of bacterium selected from the group consisting of *Campylobacter* spp., *Enterobacter* spp., *Enterococcus* spp., *Escherichia coli*,

*Gardnerella vaginalis, Haemophilis* spp., *Helicobacter pylori, Mycobacterium tuberculosis, Propionobacter acnes, Pseudomonas aeruginosa* and other *Pseudomonas* spp., *Salmonella typhimurium, Shigella* spp. and *Staphylococcus* spp.

9. The recombinant donor bacterium of claim 1, wherein the origin of replication is that of a plasmid selected from the group consisting of R6K, RK2, rts1, p15A and RSF1010.

10. The recombinant donor bacterium of claim 1, wherein the origin of replication is selected from the group consisting of F and P1.

11. The recombinant donor bacterium of claim 1, wherein the screenable marker gene confers a nutritional selection advantage on cells containing the transmissible plasmid.

12. The recombinant donor bacterium of claim 1, wherein the transfer genes are those of a plasmid selected from the group consisting of F, R6K and Ti.

13. A recombinant donor bacterium harboring at least one transmissible plasmid, said transmissible plasmid comprising:
   a) an origin of replication for synthesizing the plasmid in a bacterial cell;
   b) an origin of transfer from which conjugative transfer of the transmissible plasmid initiates from the donor bacterium to at least one recipient bacterium;
   c) at least one "killer gene" that, upon expression in a bacterial cell, produces a product that kills the cell; and
   d) at least one screenable marker gene;
   wherein the donor bacterium further comprises one or more transfer genes conferring upon the donor bacterium the ability to conjugatively transfer the transmissible plasmid to the recipient bacterium, and wherein the donor bacterium is modified so as to be unaffected by the product of the "killer gene", and further wherein the at least one recipient bacterium is a pathogenic bacterium that has not been modified so as to be affected by the product of the "killer gene".

14. The recombinant donor bacterium of claim 13, wherein the transfer genes are contained on a helper plasmid within the donor bacterium, such that the transmissible plasmid is transmissible from the donor bacterium to a recipient bacterium, but is not further self-transmissible from the recipient bacterium to another recipient bacterium.

15. The recombinant donor bacterium of claim 13, wherein the transfer genes are contained on the transmissible plasmid, such that the transmissible plasmid is self-transmissible from the donor bacterium to a recipient bacterium, and further from the recipient bacterium to another recipient bacterium.

16. The recombinant donor bacterium of claim 13, wherein the "killer gene" kills the recipient bacterium by being expressed and thereby producing a gene product that is detrimental or lethal to the recipient bacterium, and the donor bacterium has been modified so as to repress the expression of the "killer gene", thereby avoiding production of the detrimental or lethal gene product.

17. The recombinant donor bacterium of claim 13, wherein the "killer gene" is a gene of a bacteriophage.

18. The recombinant donor bacterium of claim 17, wherein the bacteriophage is selected from the group consisting of T-series phages, P1, p22 and λ.

19. The recombinant donor bacterium of claim 13, wherein the donor bacterium is a non-pathogenic strain of bacteria selected from the group consisting of *Escherichia coli, Lactobacillus* spp., *Lactococcus*, Bifidobacteria, Eubacteria, and bacterial minicells.

20. The recombinant donor bacterium of claim 13, wherein the recipient bacterium is a pathogenic strain of bacterium selected from the group *Campylobacter* spp., *Enterobacter* spp., *Enterococcus* spp., *Escherichia coli, Gardnerella vaginalis, Haemophilis* spp., *Helicobacter pylori, Mycobacterium tuberculosis, Propionobacter acnes, Pseudomonas aeruginosa* and other *Pseudomonas* spp., *Salmonella typhimurium, Shigella* spp. and *Staphylococcus* spp.

21. The recombinant donor bacterium of claim 13, wherein the origin of replication is that of a plasmid selected from the group consisting of R6K, RK2, rts1, p15A and RSF1010.

22. The recombinant donor bacterium of claim 13, wherein the origin of replication is selected from the group consisting of F and P1.

23. The recombinant donor bacterium of claim 13, wherein the screenable marker gene confers a nutritional selection advantage on cells containing the transmissible plasmid.

24. The recombinant donor bacterium of claim 13, wherein the transfer genes are those of a plasmid selected from the group consisting of F, R6K and Ti.

* * * * *